(12) United States Patent
Musheev

(10) Patent No.: US 10,603,141 B2
(45) Date of Patent: Mar. 31, 2020

(54) DENTAL IMPLANT WITH A SACRIFICIAL CORONAL PORTION

(71) Applicant: Ilia Musheev, Holon (IL)

(72) Inventor: Ilia Musheev, Holon (IL)

(*) Notice: Subject to any disclaimer, the term of this patent is extended or adjusted under 35 U.S.C. 154(b) by 11 days.

(21) Appl. No.: 15/990,760

(22) Filed: May 28, 2018

(65) Prior Publication Data

US 2018/0344433 A1 Dec. 6, 2018

(30) Foreign Application Priority Data

May 30, 2017 (IL) ...................................... IL252588

(51) Int. Cl.
*A61C 8/00* (2006.01)

(52) U.S. Cl.
CPC .......... *A61C 8/0037* (2013.01); *A61C 8/0025* (2013.01); *A61C 8/0033* (2013.01); *A61C 8/0051* (2013.01); *A61C 8/0068* (2013.01); *A61C 8/0089* (2013.01); *A61C 8/0093* (2013.01)

(58) Field of Classification Search
CPC ... A61C 8/0037; A61C 8/0025; A61C 8/0033; A61C 8/0051; A61C 8/0068; A61C 8/0089; A61C 8/0093
See application file for complete search history.

(56) References Cited

U.S. PATENT DOCUMENTS

| | | | | |
|---|---|---|---|---|
| 5,052,929 A * | 10/1991 | Seal | ........................ | A61C 8/005 433/173 |
| 5,064,373 A * | 11/1991 | Staubli | .................. | A61C 8/0048 433/173 |
| 5,125,839 A * | 6/1992 | Ingber | .................. | A61C 8/0001 433/169 |
| 5,180,303 A * | 1/1993 | Homburg | .............. | A61C 8/0048 433/173 |
| 5,201,656 A | 4/1993 | Sicurelli, Jr. | | |
| 5,447,435 A * | 9/1995 | Brodbeck | .............. | A61C 8/005 433/172 |
| 5,782,636 A * | 7/1998 | Armstrong | ........... | A61C 8/0089 408/209 |
| 6,168,436 B1 * | 1/2001 | O'Brien | .................. | A61C 8/005 433/172 |
| RE38,630 E * | 10/2004 | Lazzara | ............... | A61C 8/0089 433/165 |
| 7,780,446 B2 * | 8/2010 | Sanchez | .................. | A61C 8/005 433/173 |
| 8,529,259 B2 * | 9/2013 | Wade | .................... | A61C 8/0089 433/142 |
| 8,888,486 B2 * | 11/2014 | Goodman | .............. | A61C 8/006 433/174 |
| 9,492,248 B2 * | 11/2016 | Hori | ...................... | A61C 8/0024 |
| 9,629,699 B2 * | 4/2017 | Zipprich | .............. | A61C 8/0093 |

(Continued)

FOREIGN PATENT DOCUMENTS

WO 2015125139 8/2015

*Primary Examiner* — Nicholas D Lucchesi
(74) *Attorney, Agent, or Firm* — Preston Smirman; Smirman IP Law, PLLC

(57) ABSTRACT

A dental implant is described and includes a threaded coronal portion having a top hollow part with a cavity and an opening in a top portion of the hollow part, wherein the top hollow part is defined by sacrificial walls of the coronal portion, wherein a width of the cavity and the opening allows insertion of a cutting element of a dental saw into the cavity.

1 Claim, 2 Drawing Sheets

(56) References Cited

U.S. PATENT DOCUMENTS

| | | | |
|---|---|---|---|
| 2006/0046229 A1* | 3/2006 | Teich | A61C 8/0022 |
| | | | 433/173 |
| 2007/0099151 A1 | 5/2007 | Ilan et al. | |
| 2007/0111164 A1 | 5/2007 | Saade et al. | |
| 2008/0014555 A1* | 1/2008 | Cippiciani | A61C 8/005 |
| | | | 433/173 |
| 2008/0254414 A1* | 10/2008 | McGuire | A61C 13/0022 |
| | | | 433/223 |
| 2009/0280454 A1 | 11/2009 | Hanna | |
| 2014/0212845 A1* | 7/2014 | Wadhwani | A61C 13/08 |
| | | | 433/174 |
| 2015/0004563 A1* | 1/2015 | Blaisdell | A61C 13/34 |
| | | | 433/173 |
| 2015/0164622 A1* | 6/2015 | Odanaka | A61C 8/006 |
| | | | 433/201.1 |
| 2017/0231729 A1* | 8/2017 | Burger | A61C 8/005 |
| | | | 407/42 |

\* cited by examiner

DENTAL IMPLANT WITH A SACRIFICIAL CORONAL PORTION

CROSS-REFERENCE TO RELATED APPLICATION

The instant application claims priority to Israeli Patent Application Serial No. IL252588 filed May 30, 2017, the entire specification of which is expressly incorporated herein by reference.

FIELD OF THE INVENTION

The present invention relates generally to the field of endosseous dental implants and more specifically to the field of endosseous screw type dental implants.

BACKGROUND OF THE INVENTION

Screw type implants are implants having threaded outer surfaces and used as anchoring members for different prostheses, such as dental and orthopedic prostheses. This type of implant is screwed into a borehole arranged in the bone tissue of a bone tissue structure at a site where a prosthesis is required. The borehole may be formed into a shape generally corresponding to the shape of the implant, although slightly smaller in size. These implants may be provided with self-cutting edges to cut one or more internal threads in the inner wall of the borehole during the screwing in of the implant. If there are no self-cutting edges, the bore must be internally threaded before insertion of the implant.

Bone tissue has two components, cancellous bone tissue and cortical bone tissue. The major part of a bone usually is built up with the cancellous bone tissue, which is a relatively soft tissue in the interior of the bone. The cortical bone tissue is harder and normally forms a relatively thin layer surrounding the cancellous bone. Thus, in their final position, screw implants of the type described would typically be in contact with cancellous bone tissue along a larger part of its length, and with cortical bone tissue only at a shorter portion at one end of the implant.

When a screw type implant is in anchored position in the bone tissue, a superstructure for carrying a prosthetic part may be secured to the implant. In the case when a screw implant is used to secure a dental prosthesis, the superstructure will typically comprise an abutment or transmucosal component, which engages the implant to bridge the gingiva overlaying the maxilla or mandible at the implant site. The prosthetic part, e.g., a crown, a bridge, or a denture, is then secured to the abutment. The implant could also be formed integrally with a superstructure, such as a transgingival component, on which for example a crown is directly secured. A problem occurring when using many screw type implants is referred to as the bone resorption problem. Bone resorption is a term used for a process in which once an implant is installed in the bone tissue, the bone surrounding the implant tends to degenerate. This is highly undesired, since a diminished amount of bone surrounding the implant will lead to diminished stability and sometimes result in failure of the prosthesis. This is particularly the case because bone resorption primarily occurs in the cortical bone, which, as mentioned above, is the hardest part of the bone. Once bone resorption exists, secondary problems may also appear. Such secondary problems, particularly related to dental implants, are for example deposition of plaque, resulting in inflammation in the gingival tissue surrounding the implant, or down-growth of gingival tissue along the exposed end of the implant. Also, the aesthetic appeal of the implant is undermined by bone tissue resorption, which is an important drawback when the implant is intended for dental applications since dental prostheses form part of the field of cosmetic surgery.

SUMMARY OF THE INVENTION

According to one aspect of the present invention there is provided a dental implant having a sacrificial threaded coronal portion. In one embodiment, a dental implant of the present invention includes a sacrificial hollow part in its coronal portion. The hollow part is defined by sacrificial walls of the coronal portion of the implant. The sacrificial hollow part has a width larger than the width of a cutting element of a dental cutting tool, thus allowing insertion of the cutting element into the cavity of the hollow part through an opening in the top of the hollow part. In another embodiment of the present invention, a dental implant includes a screw that is configured to move up and down inside the implant, along the longitudinal axis of the implant, and wherein the screw head serves as a bottom of the cavity of the hollow part. The movement of the screw therefore sets the effective depth of the cavity of the hollow part.

The dental implant according to an embodiment of the present invention can be manufactured as a single piece (i.e., monolithic implant) or it can be formed from two or more pieces (i.e., modular implant).

According to another aspect of the present invention there is provided a method of adjusting the height of a dental implant installed in a jawbone. In the first step, the height of the exposed coronal portion is determined, and in the second step the exposed part of the coronal portion is saw off by a dental cutting tool (dental saw), wherein the sawing is done from inside of the cavity of the hollow part of the coronal portion of the implant.

BRIEF DESCRIPTION OF THE DRAWINGS

By way of example, embodiments of the present invention will now be described with reference to the accompanying figures of drawings in which.

DETAILED DESCRIPTION OF THE INVENTION

In the following detailed description of the invention, numerous specific details are set forth in order to provide a thorough understanding of the invention. However, it will be obvious to one skilled in the art that the invention may be used without these specific details. In other instances, well-known methods, procedures, components, and elements are not described here in detail so as not to unnecessarily obscure aspects of the invention. It will be readily understood that the components of the present invention, as generally described and illustrated in the figures, may be arranged and designed in a wide variety of different configurations. Thus, the following more detailed description of the embodiments of the devices and methods of the present invention, as represented in the figures, is not intended to limit the scope of the invention, but is merely representative of selected embodiments of the invention.

Figure 1:
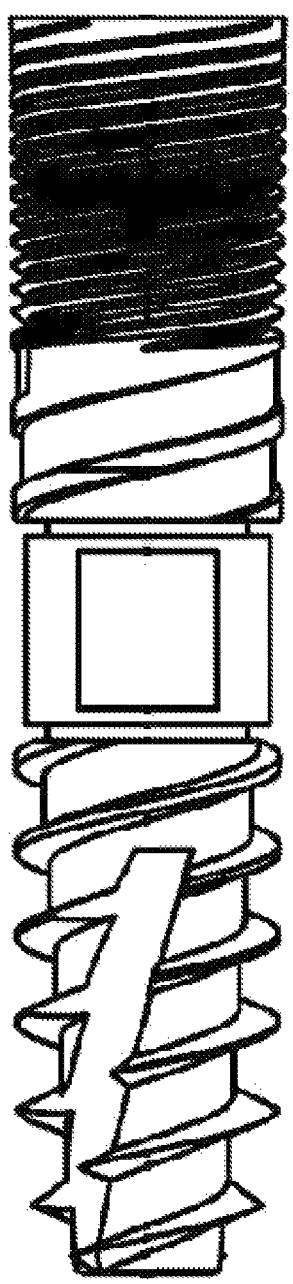
FIG. 1 is a side view of a dental implant of the present invention.
Figure 2:
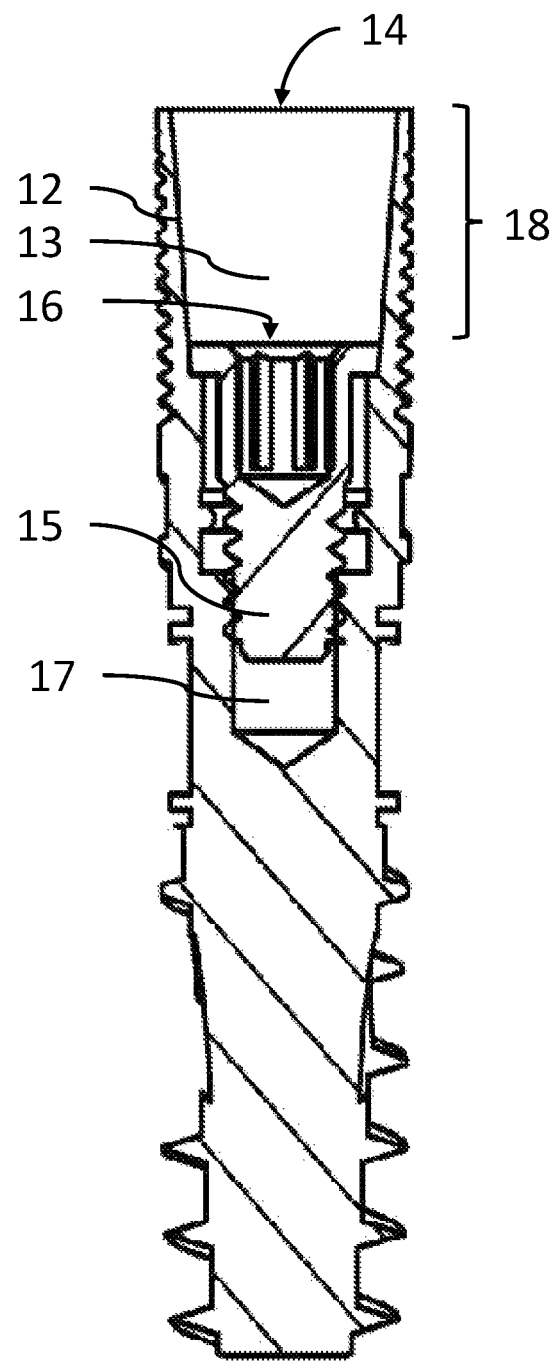
FIG. 2 is a cross-sectional side view of a dental implant of the present invention.
Figures 3, 4:
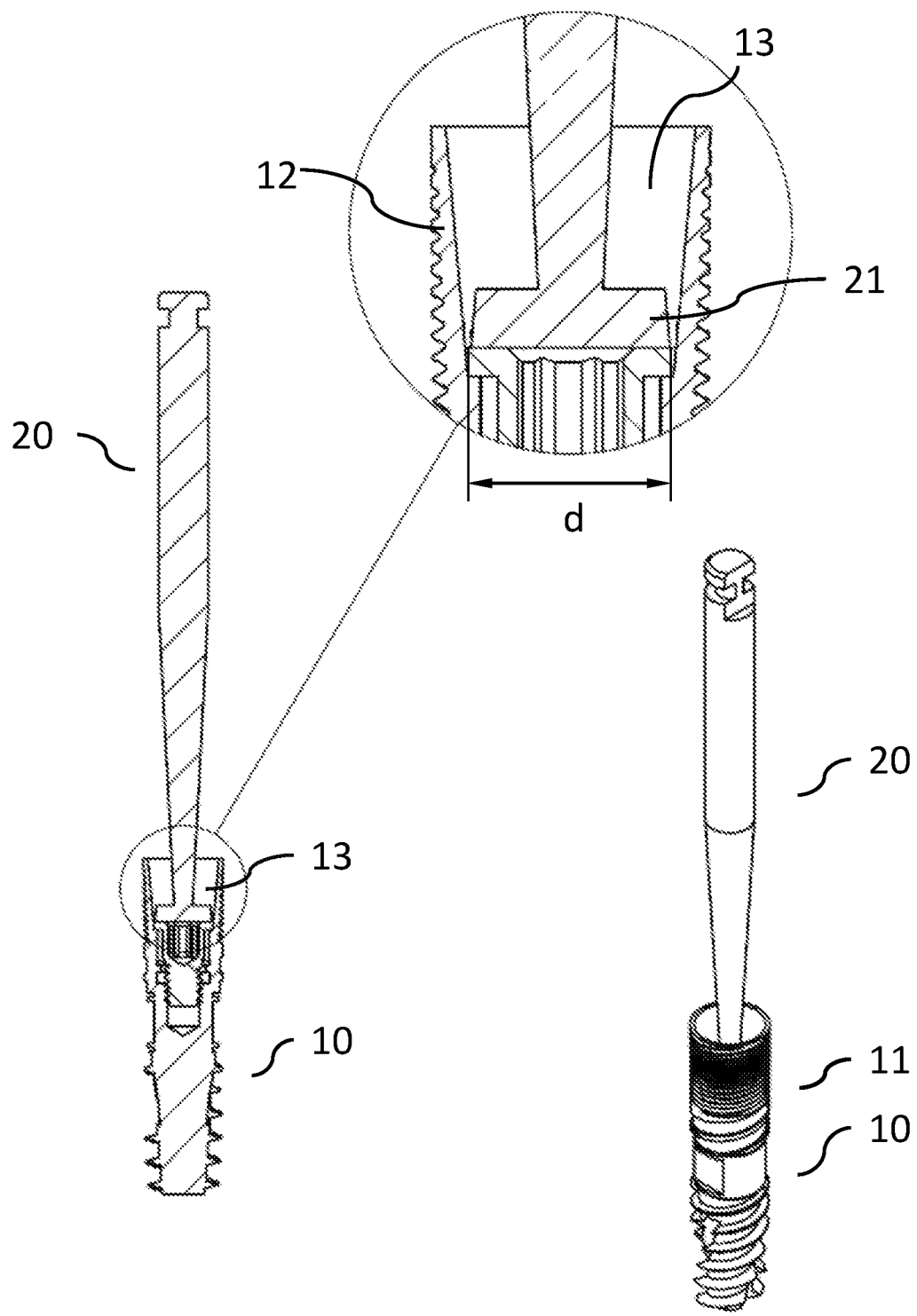
FIG. 3 is a cross-sectional side view of a dental cutting tool and a dental implant of the present invention.
FIG. 4 is a perspective view of a dental cutting tool and a dental implant of the present invention.

FIG. 1 is a side view of a dental implant 10, according to an embodiment of the invention. The dental implant 10 includes a threaded coronal portion 11, which is engaged with a cortical bone when the implant 10 is positioned inside a jawbone of a patient. The top hollow part 18 of the coronal portion 11 includes a cavity 13 and an opening 14. The opening 14 is situated at the top of the hollow part 18 of the coronal portion 11 and has a size that allows insertion of various dental tools and/or devices into the cavity 13.

Once the implant 10 is installed in a jawbone, bone resorption may occur after some time. If bone resorption occurs, it exposes a top part of the coronal portion 11 of the implant 10. Having an exposed implant is highly undesirable for esthetic reasons, and due to the deposition of plaque on the exposed surface. Therefore, it would be highly desirable to remove the exposed portion of the implant 10.

The removal of the exposed part of the coronal portion 11 of the implant 10 is done by a cutting tool (a saw) 20, which is inserted, through the opening 14, into the cavity 13 of the top hollow part 18 of the coronal portion 11. Once positioned at the desired depth inside the top hollow part 18, the cutting tool 20 cuts through the walls 12 of the coronal portion 11 and saws off the exposed part of the coronal portion 11.

The cavity 13 has a size and shape that permits insertion (through the opening 14) of the cutting tool 20 inside the coronal portion 11, while maintaining a desired orientation of a cutting element 21 of the cutting tool 20 inside the cavity 13. Preferably, the width of the cavity 13 and the opening 14 is larger than the width d of the cutting element 21.

The dental implant 10 of the present invention may be a monolithic implant (i.e., implant produced as one single piece) or it can be a modular implant.

In another embodiment of the present invention, the implant 10 may comprise a screw 15 positioned inside a threaded bore 17 of the implant 10 and configured to move along the longitudinal axis of the implant 10. The top of the screw serves as the bottom 16 of the cavity 13. Thus, the movement of the screw 15 effectively regulates the depth of the cavity 13.

The implant 10 can be manufactured from a commercially pure titanium, a titanium alloy, another biocompatible metal, or metal alloy, or ceramic, to promote osseointegration of the implant with the bone tissue of the boundary walls of the borehole.

Although illustrative embodiments have been shown and described, a wide range of modification change and substitution is contemplated in the foregoing disclosure, and in some instances, some features of the embodiments may be employed without a corresponding use of other features. Accordingly, it is appropriate that the appended claims are construed broadly and in a manner consistent with the scope of the embodiments disclosed herein.

What is claimed is:

1. A method of adjusting the height of a dental implant installed in a jawbone, comprising the steps of:
    determining the height of an exposed part of a coronal portion of the dental implant;
    inserting a dental saw into the coronal portion of the implant, through an opening at a top portion of the coronal portion; and
    sawing off the exposed part by a dental cutting tool;
    wherein the sawing is done from inside of the coronal portion.

* * * * *